United States Patent

Rollender et al.

[11] Patent Number: 4,867,316
[45] Date of Patent: Sep. 19, 1989

[54] FUNGI IDENTIFICATION KIT

[76] Inventors: William Rollender, 65 Madison St., Franklin Square, N.Y. 11010; Gordon Westermann, P.O. Box 522, Medfield, Mass. 02052

[21] Appl. No.: 189,357
[22] Filed: May 2, 1988
[51] Int. Cl.[4] .............................................. B65D 69/00
[52] U.S. Cl. ..................................... 206/570; 206/569
[58] Field of Search ......................... 206/223, 570, 569

[56] References Cited

U.S. PATENT DOCUMENTS 4,446,970  5/1984  Further ............................... 206/223
4,782,946  11/1988  Pollak .................................. 206/223

Primary Examiner—Joseph Man-Fu Moy

[57] ABSTRACT

A prepared, self-contained slide culture kit system for the identification of fungi is presentd. The kit consists of a sterile two part, clear plastic container. In the container is a block of an appropriate agar medium. The agar block is one square centimeter. In the bottom of the container is affixed a piece of absorbent material. The absorbent material acts as a sponge when dampened and provides a moist atmosphere during incubation. Over the agar block is a sterile covering. Prior to inoculation the covering of the agar block is removed. The surface of the agar block is inoculated with the fungus being identified. A sterile cover slip is placed on the surface of the agar. The absorbent material is dampened with water, the cover of the container is replaced, and the kit is incubated at the required temperature. After incubation the cover slip is removed and examined microscopically.

The Fungi Identification Kit eliminates the time consuming, and technically difficult procedures of current methods. The Kit is completely prepared, sterile, ready for use, and disposable. It is suitable for use in the clinical laboratory.

1 Claim, 1 Drawing Sheet

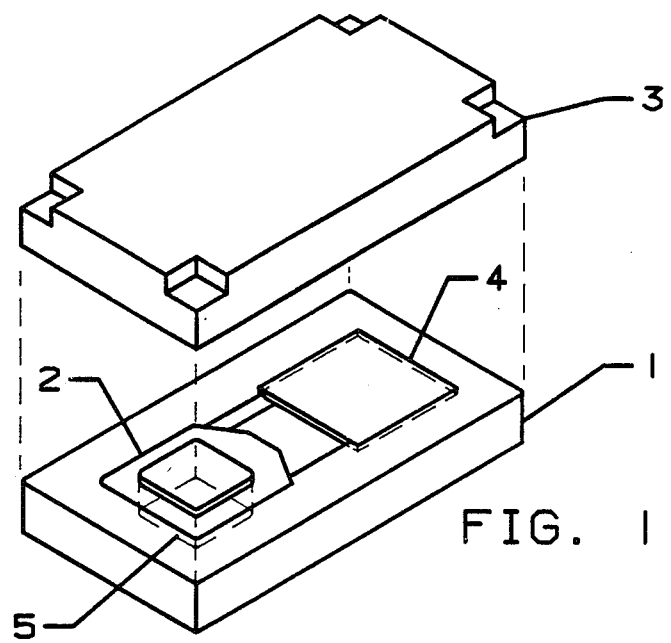
FIG. 1
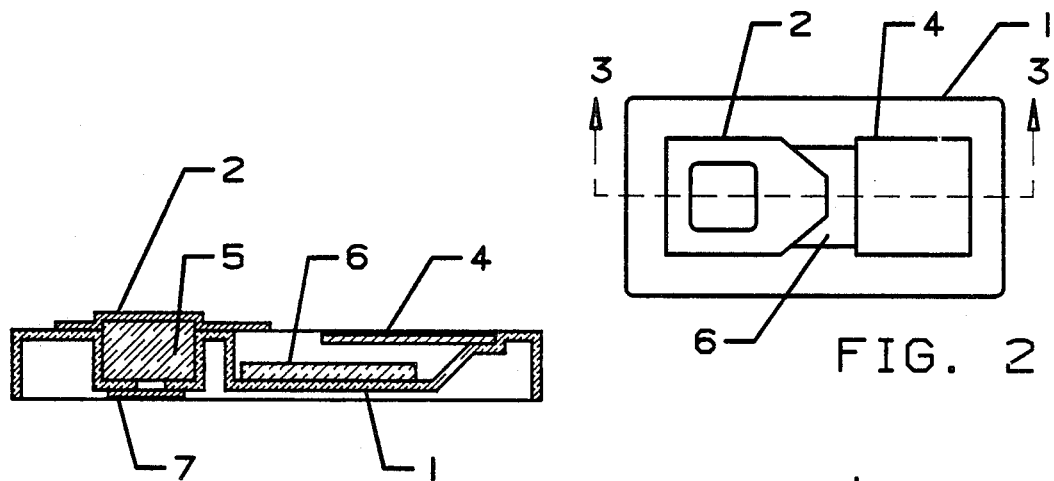
FIG. 3
FIG. 2
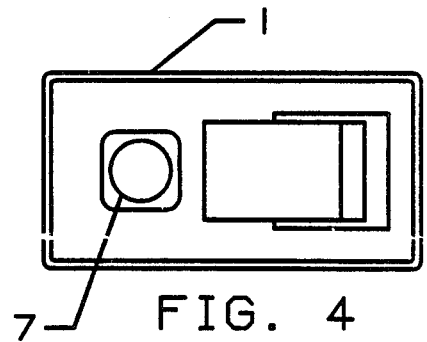
FIG. 4

FUNGI IDENTIFICATION KIT

BACKGROUND—FIELD OF INVENTION

This invention relates to the identification of filamentous fungi, molds, and yeasts, and specifically to a prepared Fungi Identification Kit.

BACKGROUND—DESCRIPTION OF PRIOR ART

Many species of fungi cause disease in man and animals. Identification of these fungi is important in establishing the etiology of the disease and in prescribing a course of treatment.

Identification of fungi is accomplished by isolating and growing these organisms on appropriate solid culture media and observing their macroscopic and microscopic appearance. Colonial morphology may be of little value in the identification of filamentous fungi due to natural variation among isolates and variation which is culture medium dependent. The definitive identification of filamentous fungi is based on the characteristic morphology of the arrangement of spores and fruiting bodies. The production of these structures is encouraged by growing these organisms on specific types of culture media. To microscopically visualize the arrangement of spores and fruiting bodies a slide culture may be done. This is accomplished by filling a petri dish with an appropriate nutrient medium such as Sabouraud's dextrose agar, corn meal agar, or potato dextrose agar. From this petri dish of agar medium a small block of agar is aseptically cut, removed and placed on a sterile slide. The agar block is inoculated on the surface with the fungus to be identified. After inoculation a sterile cover slip is placed over the top surface of the agar block. The inoculated slide-agar block is placed in an empty sterile petri dish which contains a supporting mechanism for the slide. This supporting mechanism is usually bent glass rods or wooden applicator sticks. The purpose of this is to keep the slide off of the bottom of the petri dish. In the bottom of this petri dish is a piece of dampened blotting paper. The cover is then placed on the dish. After a suitable incubation time the coverslip is removed from the agar block and placed on another slide to which a dye, such as lactophenol aniline blue, may be added. This permits the undisturbed spores to be observed microscopically as they were arranged during growth on the agar block under the coverslip.

There are many variations on this method, all requiring elaborate preparations. One is to dip a coverslip into liquid agar, allowing it to solidify and placing it on a sterile slide in a petri dish.

All current methods for growing fungi in slide cultures are based on the principle of incubation in a moist chamber. The state of the art methods require the use and construction of many components, all of which must be sterilized individually. It is laborious, time consuming, and does not allow for standardization. Contamination of the components by other organisms is frequently encountered. Most investigators, therefore, would find it desirable to have a prepared, disposable, kit which would facilitate and standardize the identification.

OBJECTS AND ADVANTAGES

Accordingly we claim the objects and advantages of the invention: to provide a prepared kit for easily; reliably; and neatly performing a slide culture for the identification of fungi. The Fungi Identification Kit is supplied completely prepared, sterile, and it is disposable. It does away with preparation and sterilization of individual components. It provides a standardized method for each test performed and eliminates all technical problems encountered in the prior art even when carried out by inexperienced technicians. It reduces the possibility of comtamination by other organisms. The kit protects the components until use.

These and other features, objects, and advantages of the invention will, in part, become obvious from the following more detailed description of the invention, taken in conjunction with the accompanying drawings which form an integral part thereof.

DRAWING FIGURES

FIG. 1 shows a perspective view of the Fungi Identification Kit with the cover displaced.
FIG. 2 shows a top view of the container.
FIG. 3 shows a section view of the container.
FIG. 4 shows a bottom view of the container.

DRAWING REFERENCE NUMERALS 1 container base plate
2 medium well cover
3 container cover plate
4 coverslip
5 culture medium well
6 hydroscopic absorbent material
7 culture medium well seal

FUNGI IDENTIFICATION KIT—DESCRIPTION

FIG. 1 is an exploded perspective view of the container according to the preferred embodiment of the invention. It is comprised of: the container base plate 1; the peel off medium well cover 2; the coverslip 4; the culture medium well 5; and the container cover plate 3 which encloses the container base plate 1.

The placement of the hydroscopic absorbent material 6 is best seen in FIG. 3. It is adhered to the container base plate 1.

The culture medium well 5 is best seen in FIG. 3. When full, it will container one square centimeter of culture medium. An aperture in the container base plate 1 permits the culture medium well 5 to be filled when the medium well cover 2 is in place.

The culture medium well seal 7 is best seen in FIG. 3 and FIG. 4. It is adhered to the container base plate 1 and covers and aperture in the culture medium well 5 after the culture medium well 5 is filled.

The container cover plate 3 is constructed slightly larger than the container base plate 1 so that when the kit is assembled it completely encloses the container base plate 1.

FIG. 4 is a bottom view of the container showing the culture medium well seal 7 covering the aperture in the culture medium well 5 in the container base plate 1.

All components of the Kit, with the exception of the absorbent material 6 and the culture medium are fabricated from a plastic material. The overall dimensions of the assembled container are approximate eight centimeters by five centimeters by one and a half centimeters.

FUNGI IDENTIFICATION KIT—OPERATION

The absorbent material 6 is cellulose acetate and is adhered to the container base plate 1. The culture medium well cover 2 is adhered to the container base base plate 1 over the culture medium well 5. The container base plate 1 is so designed to allow the coverslip 4 to snap firmly in place. The container cover plate 3 is placed over the container base plate 1 and the Kit is sterilized by ethylene oxide.

Agar, as a solidifying agent in culture media formulation, has the unique characteristic of existing in the liquid state at one hundred degrees and in the solid state at forty five degrees centrigrade. The appropriate agar medium for the fungus identification is prepared according to the formula. The media is heated to one hundred degrees centigrade to dissolve the agar and then sterilized in a closed container by autoclaving with steam under pressure. The medium is prevented from solidifying by keeping it a constant fifty degrees centigrade with a heated water bath.

After sterilization the Kit is inverted so that it is resting on the container cover plate 3 and the culture medium well 5 is filled with the liquid medium through the aperture in the container base plate 1. In this fashion the liquid medium will completely fill the culture medium well 5. The kit is allowed to remain undisturbed in the inverted position until the temperature of the agar medium falls to forty five degrees centigrade and the medium solidifys. The culture medium wall seal 7 is then adhered over the filling aperture in the container base plate 1. This novel method of filling the culture medium well 5 has the distinct advantage of eliminating a meniscus on the top surface of the agar block under the medium well cover 2. This allows for a completely flat surface on the agar block when the medium well cover 2 is removed prior to inoculation. A flat surface is essential so that the cover slip will remain in contact with the agar block at all times.

The medium well cover 2 is designed so that after removal a small portion of the agar block extends above the container base plate 1. This allows ambient air to circulate around the agar block after inoculation and the cover slip 4 is placed on top. This creates aerobic conditions for the growing fungus.

The medium well cover 2 is removed by peeling it back. The exposed surface of the agar block is inoculated with the fungus to be identified. This is done by placing a small specimen of the fungus on the surface of the agar block. The cover slip 4 is removed from its position in the container base plate 1 and placed on top of the inoculated agar block. The cellulose acetate absorbent material 6 is moistened with water. This will provide a moist atmosphere during incubation and prevent water loss from the agar block.

The container cover plate 3 is replaced and the kit is incubated at the required temperature.

After a suitable incubation time has elapsed the container cover plate 3 is removed and the fungi can be observed microscopically by placing the entire Kit on the microscope stage and viewing it through the coverslip. Observing the fungi in this manner negates the premature removal of the coverslip if adequate growth for identification has not occured. If so desired, the coverslip may be removed from the agar block placed on a slide and examined microscopically.

CONCLUSION, RAMIFICATIONS AND SCOPE OF INVENTION

Thus the reader will see that the Fungi Identification Kit provides a novel system for the identification of fungi. It is completely prepared, sterile, ready for use, and disposable. It eliminates time consuming and technical difficulties experienced in prior methods. The use of the Kit standardizes the identification of fungi. It minimizes the possibility of contamination by other organisms and greatly simplifies the identification procedure.

While my above description contains many specifications, these should not be construed as limitations on the scope of the invention, but rather as an exemplification of one preferred embodiment thereof. Those skilled in the art will envision many other possible variations that are within its scope. For example, skilled artisans will readily be able to change the dimensions and shapes of the various embodiments. They will also be able to make the container, depicted in FIG. 1, of alternative plastic materials. They can make many variations on the size and shape of the container in FIG. 1. Variations can also be made on the size or shape of the culture medium well shown in FIG. 3. A variation in size or shape of the culture medium well would change the shape of the agar block. For example, the resulting agar block may be round instead of square. Accordingly, the coverslip, shown in FIG. 1 and FIG. 2 would also be round. The absorbent material shown in FIG. 3 may be of a material other than cellulose acetate. Accordingly, the scope of the invention should be determined not by the embodiments illustrated, but by the appended claims and their legal equivalents.

We claim:

1. A prepared, disposal Kit system for the identification of fungi comprising:
    a sterile, two part, clear plastic container having a top section and a base section, and when assembled has the approximate dimensions of eight centimeters by five centimeters by one and one half centimeters:
    said base section having a hydroscopic material adhered to it, a culture medium well which is filled with an appropriate agar medium, a coverslip, a culture medium well seal;
    said culture medium well is filled in a unique manner through an aperature in the underside of the base section, thus eliminating a meniscus on top of the agar block;
    said top section is so constructed that it encloses the bottom section.

* * * * *